United States Patent
Tierney et al.

(10) Patent No.: US 7,329,896 B2
(45) Date of Patent: *Feb. 12, 2008

(54) POLYMERIZABLE CHARGE TRANSPORT COMPOUNDS

(75) Inventors: Steven Tierney, Southampton (GB); Mark Goulding, Ringwood (GB); Louise Farrand, Spetisbury, Blandford Forum (GB); Mark Giles, Southampton (GB); Marcus Thompson, Fordingbridge (GB); Maxim Shkunov, Southampton (GB); David Sparrowe, Bournemouth (GB); Iain McCulloch, Kings Somborne (GB); Martin Heeney, Bassett (GB)

(73) Assignee: Merck Patent GmbH, Darmstadt (DE)

( * ) Notice: Subject to any disclaimer, the term of this patent is extended or adjusted under 35 U.S.C. 154(b) by 354 days.

This patent is subject to a terminal disclaimer.

(21) Appl. No.: 10/482,937

(22) PCT Filed: Jun. 12, 2002

(86) PCT No.: PCT/EP02/06442

§ 371 (c)(1),
(2), (4) Date: Jan. 6, 2004

(87) PCT Pub. No.: WO03/006468

PCT Pub. Date: Jan. 23, 2003

(65) Prior Publication Data

US 2004/0175638 A1    Sep. 9, 2004

(30) Foreign Application Priority Data

Jul. 9, 2001    (EP) .................................. 01115740

(51) Int. Cl.
*H01L 29/12* (2006.01)
*H01L 51/30* (2006.01)
*C09K 19/58* (2006.01)
*C09K 19/38* (2006.01)
*C09K 19/52* (2006.01)

(52) U.S. Cl. ................. 257/40; 252/299.01; 252/299.3; 428/1.1; 428/620

(58) Field of Classification Search ................. 428/1.1, 428/620; 252/299.01, 299.62, 299.63, 299.5, 252/299.3, 500; 257/40

See application file for complete search history.

(56) References Cited

U.S. PATENT DOCUMENTS

| | | | |
|---|---|---|---|
| 5,723,066 A * | 3/1998 | Coates et al. ........... | 252/299.01 |
| 6,676,857 B2 * | 1/2004 | Heeney et al. .............. | 252/500 |
| 6,695,978 B2 * | 2/2004 | Worrall et al. ......... | 252/299.62 |
| 6,800,763 B2 * | 10/2004 | Farrand et al. ............... | 549/50 |
| 6,805,922 B2 * | 10/2004 | Heeney et al. .............. | 428/1.1 |
| 6,806,374 B2 * | 10/2004 | Heeney et al. ................. | 549/59 |
| 6,824,706 B2 * | 11/2004 | Heeney et al. ......... | 252/299.01 |
| 6,841,677 B2 * | 1/2005 | Heeney et al. ................. | 546/80 |
| 6,863,841 B2 * | 3/2005 | Kirsch et al. .......... | 252/299.61 |
| 2003/0047719 A1 * | 3/2003 | Heeney et al. .............. | 252/500 |
| 2003/0047720 A1 * | 3/2003 | Heeney et al. .............. | 252/500 |
| 2003/0062509 A1 * | 4/2003 | Heeney et al. ......... | 252/299.61 |
| 2003/0062536 A1 * | 4/2003 | Heeney et al. ........... | 257/183.1 |
| 2003/0067267 A1 * | 4/2003 | Heeney et al. .............. | 313/504 |
| 2003/0085381 A1 * | 5/2003 | Worrall et al. ......... | 252/299.61 |
| 2003/0166943 A1 * | 9/2003 | Kirsch et al. ............... | 548/143 |
| 2004/0119049 A1 * | 6/2004 | Heeney et al. ........... | 252/299.3 |
| 2004/0127592 A1 * | 7/2004 | Heeney et al. ................. | 522/6 |
| 2004/0176560 A1 * | 9/2004 | Heeney et al. ................. | 528/4 |
| 2004/0230021 A1 * | 11/2004 | Giles et al. ..................... | 528/4 |

OTHER PUBLICATIONS

R. Kiebooms et al., "Synthesis, Electrical, and Optical Properties of Conjugated Polymers", *Handbook of Advanced Electronics and Photonic Materials and Devices*, vol. 8, pp. 1-102 (2001).
G. Kossmehl, et al., "Uber Polyarylenalkenylene und Polyheteroarylenalkenylene", *Makromolekulare Chemie, Macromolecular Chemistry and Physics*, Huthig und Wepf Verlag, Basel, Ch, vol. 183, No. 11, pp. 2771-2786 (Nov. 1, 1982).
D. Haristoy, et al., "Structure and Photoconductive Behaviour of a Sanidic Liquid Crystal", *Liquid Crystals*, vol. 27, No. 3, pp. 321-328 (Mar. 2000).

* cited by examiner

*Primary Examiner*—Shean C Wu
(74) *Attorney, Agent, or Firm*—Millen, White, Zelano & Branigan, PC

(57) ABSTRACT

The invention relates to polymerizable charge transport compounds, their use as semiconductors or charge transport materials, in optical, electrooptical or electronic devices like for example organic field effect transistors (FET or OFET) for thin film transistor liquid crystal displays and integrated circuit devices such as RFID tags, electroluminescent devices in flat panel displays, and in plotovoltaic and sensor devices, and to a field effect transistor, light emitting device or ID tag comprising the polymerisable charge transport compounds.

30 Claims, No Drawings

POLYMERIZABLE CHARGE TRANSPORT COMPOUNDS

FIELD OF INVENTION

The invention relates to polymerisable charge transport compounds and to their use as semiconductors or charge transport materials, in optical, electrooptical or electronic devices like for example organic field effect transistors (FET or OFET) for thin film transistor liquid crystal displays and integrated circuit devices such as RFID tags, electroluminescent devices in flat panel displays, and in photovoltaic and sensor devices. The invention further relates to a field effect transistor, light emitting device or ID tag comprising the polymerisable charge transport compounds.

BACKGROUND AND PRIOR ART

Organic materials have recently shown promise as the active layer in organic based thin film transistors and organic field effect transistors (FET, OFET) [see H. E. Katz et al., *Acc. Chem. Res.*, 2001, 34, 5, 359]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semiconducting material and the current on/off ratio, so the ideal semiconductor should have a low conductivity in the off state, combined with a high charge carrier mobility ($>1\times10^{-3}$ cm$^2$ V$^{-1}$ s$^{-1}$). In addition, it is important that the semiconducting material is relatively stable to oxidation i.e. it has a high ionisation potential, as oxidation leads to reduced device performance.

A known compound which has been shown to be an effective p-type semiconductor for OFETs is pentacene [see S. F. Nelson et al., *Appl. Phys. Lett.* 1998, 72, 1854] which has a planar, highly delocalised pi electron system, essential for good semiconducting properties such as charge carrier mobility. When deposited as a thin film by vacuum deposition, it was shown to have carrier mobilities in excess of 1 cm$^2$ V$^{-1}$ s$^{-1}$ with very high current on/off ratios greater than 10$^6$. However, vacuum deposition is an expensive processing technique that is unsuitable for the fabrication of large-area films.

One requirement for large scale, low cost manufacture is that fabrication steps be carried out by solution processing. This allows the possibility for roll-to-roll processing, where large areas can be coated and printed at high speed. Key requirements for this technique is that the material has sufficient solubility in a process appropriate solvent to ensure that the solution wets and coats the surface, and that the film formed is coherent. In addition, for a multilayer structure, it is essential that the solvent used in deposition of a layer does not effect the layer on which it is in contact with. As each layer is applied via solution, then a solvent with an incompatible solubility parameter to the previous layer is required. This solvent parameter latitude can be significantly widened if the previous layer can undergo a chemical process such as crosslinking, which effectively eliminates solubility an any subsequent processing solvent.

It has also been shown that [see Sirringhaus Appl. Phys. Lett., 77(3) (2000) 406-408] molecular self organisation into well ordered macro domains, as can be achieved in the liquid crystalline phase, also improves charge carrier mobility. Utilisation of a liquid crystal phase to both order and align molecules in a preferred orientation and direction is therefore advantageous in optimisation of semiconducting properties. In order to align and order during processing timescales and temperatures, small molecules are preferred, although polymers offer stability advantages.

It was an aim of the present invention to provide new organic materials for use as semiconductors or charge transport materials, which satisfy all criteria discussed in that they are easy to synthesize, have high charge mobility through molecular orbital delocalisation through an oxidatively stable pi conjugated system, can be oriented and aligned during processing to form a closely packed, stable morphology, and is ammeanable to a multilaminar solution process. The materials should be therefore be easily processible to form thin and large-area films for use in semiconductor-devices. Other aims of the invention are immediately evident to the skilled in the art from the following description.

The inventors have found that these aims can be achieved by providing polymerisable compounds having two or more polymerisable groups that are attached optionally via spacer groups, to a core imparting charge transport properties to the compound. These compounds are more effective than conventional organic materials (conjugated oligomers and polymers) as charge transport materials due to the following features. Firstly, the highly ordered nature of the mesogenic compounds in the mesophase (for example in the smectic phase) will result in a denser, more closely packed structure than an amorphous polymer, facilitating intermolecular charge-hopping mechanisms and so increasing charge carrier mobilities. Furthermore, the polymerisable end-groups can be crosslinked to freeze the ordering of the mesophase in the structure, and densify the structure even further. Compared to standard mesogenic materials, crosslinked materials obtained from the polymerisable compounds of the present invention have improved thermal and solvent resistance, and are thus impervious to further solution processing steps that are necessary for the fabrication of an electronic device.

A further aspect of the invention relates to liquid crystal polymers, in particular liquid crystal side chain polymers obtained from the reactive mesogens according to the present invention, which are then further processed e.g. from solution as thin layers for use in semiconductor devices.

JP2000-347432-A and JP11-209761 describe liquid crystal charge transport materials having a polymerisable group that can be polymerised to form polymer films. However, they do not disclose compounds with more than one polymerisable group.

Grell et al., *J. Korean Phys. Soc.* 2000, 36(6), 331 suggest a reactive mesogen comprising a conjugated distyrylbenzene core with two reactive acrylate end groups as a model compound for molecular electronics. However, there is no disclosure if the shown compound has suitable charge transport properties, or how it can be processed to form a device.

Definition of Terms

The terms 'liquid crystalline or mesogenic material' or 'liquid crystalline or mesogenic compound' means materials or compounds comprising one or more mesogenic groups, for example rod-shaped, lath-shaped or disk-shaped groups, i.e. groups with the ability to induce liquid crystal phase behaviour. The compounds or materials comprising mesogenic groups do not necessarily have to exhibit a liquid crystal phase themselves. It is also possible that they show liquid crystal phase behaviour only in mixtures with other compounds, or when the mesogenic compounds or materials, or the mixtures thereof, are polymerised.

The term 'polymerisable' includes compounds or groups that are capable of participating in a polymerisation reaction, like radicalic or ionic polymerisation from unsaturated functionality, polyaddition or polycondensation, and reactive compounds or reactive groups that are capable of being grafted for example by condensation or addition to a polymer backbone in a polymeranaloguous reaction.

The term 'film' includes self-supporting, i.e. free-standing, films that show more or less pronounced mechanical stability and flexibility, as well as coatings or layers on a supporting substrate or between two substrates.

SUMMARY OF THE INVENTION

One object of the invention are polymerisable charge transport compounds comprising a group containing a delocalised pi-electron unit that imparts charge transport capability to the compounds, and further comprising two or more polymerisable groups that are optionally linked to the group containing the delocalised pi-electron unit via flexible spacer groups.

Especially preferred are polymerisable charge transport compounds of formula I

wherein
P is a polymerisable or reactive group,
Sp is a spacer group or a single bond,
a is an integer $\geq 2$, and
T is a group containing a delocalised pi-electron unit that imparts charge transport capability to the compound of formula I.

Another object of the invention is a compound of formula I wherein T is in addition a mesogenic group or comprises a mesogenic group.

Another object of the invention is a polymerisable liquid crystal material comprising one or more compounds of formula I and optionally comprising one or more further polymerisable compounds, wherein at least one of the compounds of formula I and the further polymerisable compounds is mesogenic or liquid crystalline.

Another object of the present invention is an anisotropic polymer film with charge transport properties obtainable from a polymerisable liquid crystal mixture as defined above that is aligned in its liquid crystal phase into macroscopically uniform orientation and polymerised or crosslinked to fix the oriented state.

Another object of the invention is a liquid crystal side chain polymer (SCLCP) obtained from a polymerisable liquid crystal material as defined above by polymerisation or polymeranaloguous reaction. Particularly preferred are SCLCPs obtained from one or more compounds according to formula I or from a polymerisable mixture comprising one or more compounds of formula I.

Another object of the invention is an SCLCP obtained from one or more compounds of formula I or from a polymerisable liquid crystal mixture as defined above, by copolymerisation or polymeranaloguous reaction together with one or more additional mesogenic or non-mesogenic comonomers.

Another object of the invention is the use of compounds of formula I and mixtures or polymer films obtained thereof as semiconductors or charge transport materials, in particular in optical, electrooptical or electronic devices, like for example in field effect transistors (FET) as components of integrated circuitry, as thin film transistors in flat panel display applications or for Radio Frequency Identification (RFID) tags, or in semiconducting components for organic light emitting diode (OLED) applications such as electroluminescent displays or backlights of e.g. liquid crystal displays, for photovoltaic or sensor devices, as electrode materials in batteries, as photoconductors and for electrophotographic applications like electrophotographic recording.

Another object of the invention is a field effect transistor, for example as a component of integrated circuitry, as a thin film transistor in flat panel display applications, or in a Radio Frequency Identification (RFID) tag, comprising one or more compounds of formula I or a mixture or polymer film obtained thereof.

Another object of the invention is a semiconducting component, for example in OLED applications like electroluminescent displays or backlights of e.g. liquid crystal displays, in photovoltaic or sensor devices, as electrode materials in batteries, as photoconductors and for electrophotographic applications, comprising one or more compounds of formula I or a mixture or polymer film obtained thereof.

Another object of the invention is a security marking or device comprising an RFID or ID tag or a FET according to the invention.

DETAILED DESCRIPTION OF THE INVENTION

The compounds of formula I provide several advantages over prior art materials
- by adding substituent chains and other groups they can be made more soluble, thus being suitable for spin coating or solution coating techniques, rather than vacuum deposition, to prepare thin films for use e.g. in electronic devices such as transistors,
- they can be made mesogenic or liquid crystalline, thus exhibiting a higher degree of order that leads to particularly high charge carrier mobility, in particular when being aligned in their meosphase into macroscopically uniform orientation
- their macroscopic ordered, oriented and aligned microstructures can be frozen in by in situ polymerisation leading to long range monodomain morphology,
- due to the presence of two or more polymerisable groups they can be crosslinked to form coherent polymer films with high thermal, mechanical and chemical stability,
- they combine the properties of a semiconducting material with those of a mesogenic material to give novel materials with a rigid, planar conjugated core and a flexible chain to increase solubility and to decrease the melting point, which show high charge carrier mobility when being aligned in their mesophase.

The compounds of formula I are useful as charge transport semiconductors. They have high carrier mobilities and good current or/off ratios. In particular, the introduction of alkyl or fluoroalkyl side chains to the group T improves the solubility and therefore the solution processibility of the compounds of formula I. Furthermore, the presence of fluoroalkyl side chains also renders these compounds effective as n-type semiconductors. The electron-withdrawing nature of the fluoroalkyl substituents will also lower the HOMO further and result in a more stable material, which is less susceptible to oxidation.

Particularly preferred are mesogenic or liquid crystalline compounds of formula I, wherein T is a mesogenic group. These compounds are particularly useful as semiconductors or charge transport materials, as they can be processed while in the highly ordered mesophase morphology, and readily aligned by conventional techniques in a preferred direction. Both smectic and nematic mesophase ordering allows close packing of molecular pi-electron systems, which maximises intermolecular charge transfer which occurs through a hopping mechanism between adjacent molecules. This ordered, and oriented microstructure can be permanently "frozen-in" by polymerising the mesogens, which can also create a structure with long range order, or "monodomain". Formation of a monodomain also maximises charge transfer by eliminating charge trap sites at grain boundaries, while the polymerisation also improves the mechanical properties of the film. Further, by crosslinking the mesogens, a highly stable structure results, which has an additional advantage of being impervious to subsequent processing solvents during device fabrication, thus allowing a wider range of solvents to be used in deposition of the next layer of the device by solution techniques. In addition, it is often observed that this crosslinking further densifies the film, leading to smaller intermolecular distances and improved charge transport.

Side chain liquid crystal polymers or copolymers (SCLCPs), in which the semiconducting component is located as a pendant group, separated from a flexible backbone by an aliphatic spacer group, offer the possibility to obtain a highly ordered lamellar like morphology. This structure consists of closely packed conjugated aromatic mesogens, in which very close (typically <4 Å) pi-pi stacking can occur. This stacking allows intermolecular charge transport to occur more easily, leading to high charge carrier mobilities. SCLCPs are advantageous for specific applications as they can be readily synthesized before processing and then e.g. be processed from solution in an organic solvent. If SCLCPs are used in solutions, they can orient spontaneously when coated onto an appropriate surface and when at their mesophase temperature, which can result in large area, highly ordered domains.

It is also possible to copolymerise compounds of formula I via group P with other polymerisable mesogenic or liquid crystal monomers that are known from prior art, in order to induce or enhance liquid crystal phase behaviour.

Particularly preferred are liquid crystal compounds of formula I, or liquid crystal mixtures comprising one or more compounds of formula I, that exhibit a nematic and/or smectic liquid crystal phase. For FET applications smectic materials are especially preferred. For OLED applications nematic or smectic materials are especially preferred.

Especially preferred are compounds having 2, 3, 4, 5 or 6, very preferably 2 or 3 polymerisable groups P. Further preferred are compounds comprising more than 2 polymerisable groups.

Especially preferred compounds of formula I are those wherein a is 2, 3, 4, 5 or 6, further those wherein a >2, preferably 3, 4, 5 or 6.

T in formula I is preferably a rod-shaped, lath-shaped or disk-shaped mesogenic group. Compounds having a disk-shaped group exhibit discotic liquid crystal phases wherein the molecules are stacked to form columnar structures, with a high charge carrier mobility in the direction parallel to the columns.

In a preferred embodiment of the present invention T is a group selected of formula II

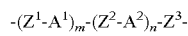   II wherein $A^1$ is, in case of multiple occurrence independently of each other, an aromatic or heteroaromatic group, or a partially saturated alicyclic or heterocyclic group that is capable of forming a conjugated pi-electron system, having up to 25 C atoms and being unsubstituted or mono-or polysubstituted with R, $A^2$ has one of the meanings of $A^1$ or is, in case of multiple occurrence independently of each other, a saturated alicyclic or heterocyclic group with up to 25 C atoms which is unsubstituted, mono- or polysubstituted with R, $Z^1$ to $Z^3$ are independently of each other —O—, —S—, —CO—, —COO—, —OCO—, —O—COO—, —CO—$NR^0$—, —$NR^0$—CO—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —$CX^1$=$CX^2$—, —C≡C—, —CH=CH—COO—, —OCO—CH=CH— or a single bond, $X^1$ and $X^2$ are independently of each other H, F, Cl or CN, R is H, halogen, CN, $NO_2$, straight chain, branched or cyclic alkyl with 1 to 20 C-atoms, which may be unsubstituted, mono- or poly-substituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, an aromatic or heteroaromatic group, or denotes P-Sp, $R^0$ and $R^{00}$ are independently of each other H or alkyl with 1 to 12 C-atoms, m is 1, 2 or 3, and n is 0, 1, 2 or 3.

R is preferably optionally fluorinated alkyl or alkoxy with 1 to 15 C atoms. Further preferred are compounds wherein one or more groups R denote P-Sp.

Particularly preferred groups T are those wherein $Z^1$, $A^1$, $Z^2$, $A^2$ and $Z^3$ together form a conjugated pi-electron system. Therein, $A^1$ and $A^2$ are preferably arylene or heteroarylene and $Z^1$, $Z^2$ and $Z^3$ are preferably a single bond or an unsaturated group like for example —C≡C— or —$CX^1$=$CX^2$—.

Further preferred groups T are those of the following formulae

   II1

   II2

   II3

   II4

   II5

   II6

   II7

   II8

   II9 wherein $Z^1$, $Z^2$, $Z^3$, $A^1$ and $A^2$ and $T^1$ have in each case independently one of the meanings of formula II.

$A^1$ is preferably 1,4-phenylene-in which, in addition, one or more CH groups may be replaced by N one or two non-adjacent $CH_2$ groups may be replaced by O and/or S, thiophene-2,5-diyl, thienothieophene-2,5-diyl, dithienothiophene-2,6-diyl, or, naphthalene-2,6-diyl, it being possible for all of these groups to be unsubstituted, mono-or polysubstituted by L, with L being halogen, CN, SCN, $NO_2$, $SF_5$ or an alkyl, alkoxy, alkylcarbonyl or alkoxycarbonyl group with 1 to 12 C atoms, wherein one or more H atoms may be substituted with F or Cl.

$A^2$ preferably has one of the preferred meanings of $A^1$ given above.

$A^1$ and $A^2$ are particularly preferably 1,4-phenylene that is substituted with 1, 2 or 3 groups L as defined above, or thiophene-2,5-diyl, thienothieophene-2,5-diyl or dithienothiophene-2,6-diyl all of which are optionally substituted with one or more groups L as defined above.

$Z^{1-3}$ are preferably selected from —O—, —S—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —$CX^1$=$CX^2$—, —C≡C— and a single bond, in particular from —CH=N—, —N=CH—, —N=N—, —CH=$CR^0$—, —$CX^1$=$CX^2$—, —C≡C— and a single bond.

In another preferred embodiment of the present invention, T is a disk-shaped group, selected for example from the group comprising phthalocyanines or their heterocyclic analogues, triphenylenes, phenanthrenes, perylenes, perylene imides, porphyrins, decacyclenes or tricyclochinazolines, all of which may be substituted or unsubstituted by organic groups. All these groups and their synthesis are known from the literature and are described for example in WO 95/17018, WO 95/04306, EP 0 527 376 or U.S. Pat. No. 5,736,068 or the references cited therein.

In the foregoing and the following, aromatic and heteroaromatic groups are preferably mono-, bi-or tricyclic groups with up to 25 C atoms that may also comprise condensed rings and are optionally substituted with one or more groups R. Very preferred aromatic and heteroaromatic groups are those having one of the preferred meanings of $A^1$ as given above and below.

—$CX^1$=$CX^2$— is preferably —CH=CH—, —CH=CF—, —CF=CH—, —CF=CF—, —CH=C(CN)— or —C(CN)=CH—.

R in formula I is preferably H, F, Cl or straight chain, branched or cyclic alkyl with 1 to 20 C-atoms, which may be unsubstituted, mono- or poly-substituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, or an aromatic or heteroaromatic group.

Very preferably R is selected from $C_1$-$C_{20}$-alkyl, $C_1$-$C_{20}$-fluoroalkyl, $C_1$-$C_{20}$-alkenyl, $C_1$-$C_{20}$-alkynyl, $C_1$-$C_{20}$-alkoxy, $C_1$-$C_{20}$-thioether, $C_1$-$C_{20}$-silyl, $C_1$-$C_{20}$-ester and $C_1$-$C_{20}$-amino.

If R is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy,-undecoxy, dodecoxy, tridecoxy or tetradecoxy, for example. Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

Halogen is preferably F or Cl.

The polymerisable or reactive group P is preferably selected from $CH_2$=$CW^1$—COO—,

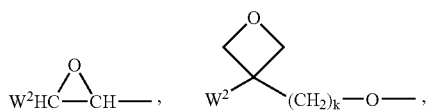

$CH_2$=$CW^2$—(O)$_{k1}$—, $CH_3$—CH=CH—O—, HO—$CW^2W^3$—, HS—$CW^2W^3$—, $HW^2N$—, HO—$CW^2W^3$—NH—, $CH_2$=$CW^1$—CO—NH—, $CH_2$=CH—(COO)$_{k1}$—Phe-(O)$_{k2}$—, Phe-CH=CH—, HOOC—, OCN— and $W^4W^5W^6Si$—, with $W^1$ being H, Cl, CN, phenyl or alkyl with 1 to 5 C-atoms, in particular H, Cl or $CH_3$, $W^2$ and $W^3$ being independently of each other H or alkyl with 1 to 5 C-atoms, in particular methyl, ethyl or n-propyl, $W^4$, $W^5$ and $W^6$ being independently of each other Cl, oxaalkyl or oxacarbonylalkyl with 1 to 5 C-atoms, Phe being 1,4-phenylene and $k_1$ and $k_2$ being independently of each other 0 or 1.

Especially preferred groups P are $CH_2$=CH—COO—, $CH_2$=C($CH_3$)—COO—, $CH_2$=CH—, $CH_2$=CH—O— and

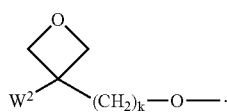

Very preferred are acrylate and oxetane groups. Oxetanes produce less shrinkage upon polymerisation (cross-linking), which results in less stress development within films, leading to higher retention of ordering and fewer defects. Oxetane cross-linking also requires cationic initiator, which unlike free radical initiator is inert to oxygen.

As for the spacer group Sp all groups can be used that are known for this purpose to those skilled in the art. The spacer group Sp is preferably of formula S—X, wherein S is alkylene with up to 20 C atoms which may be unsubstituted, mono- or poly-substituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, X is —O—, —S—, —CO—, —COO—, —OCO—, —O—COO—, —CO—$NR^0$—, —$NR^0$—CO—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH=N—, —N=CH—, —N=N—, —CH=$CR^0$—, —CX¹=CX²—, —C≡C—, —CH=CH—COO—, —OCO—CH=CH— or a single bond, and R⁰ and R⁰⁰ have one of the meanings given above.

X is preferably —O—, —S—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR⁰—, —CX¹=CX²—, —C≡C— or a single bond, in particular —O—, —S—, —C≡C—, —CX¹=CX²— or a single bond, very preferably a group that is capable to form a conjugated system, like for example —C≡C— or —CX¹=CX²—, or a single bond.

In case the group P—S—X is linked to a group $Z^1$ or $Z^3$, one of X and $Z^1$ or $Z^3$ is preferably a single bond.

Typical spacer groups S are for example —(CH$_2$)$_p$—, —(SiR⁰R⁰⁰—O)$_p$—, —(CH$_2$CH$_2$O)$_r$—CH$_2$CH$_2$—, —CH$_2$CH$_2$—S—CH$_2$CH$_2$— or —CH$_2$CH$_2$—NH—CH$_2$CH$_2$—, with p being an integer from 2 to 12, r being an integer from 1 to 3 and R⁰ and R⁰⁰ having the meanings given above.

Preferred spacer groups S are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

In case of compounds of formula I with more than one group P-Sp, the spacer groups Sp and/or the polymerisable groups P can be identical or different.

Further preferred are compounds with one or more groups P-Sp wherein Sp is a single bond.

SCLCPs obtained from the inventive compounds or mixtures by polymerisation or copolymerisation have a backbone that is formed by the polymerisable group P in formula I.

Another preferred embodiment of the present invention relates to compounds having a branched polymerisable group carrying two or more reactive moieties. These compounds are preferably selected of formula I'

(P')$_b$-T     I' wherein b is ≧1, T has the meaning of formula I and P' is a branched polymerisable group carrying two or more reactive moieties.

b is preferably 1, 2, 3 or 4, in particular 1 or 2.

T is preferably selected of formula II'

-(Z¹-A¹)$_m$-(Z²-A²)$_n$-Z³-R'     II' wherein $Z^{1-3}$, A¹, A², m and n have the meanings of formula II or the preferred meanings given above, R' has one of the meanings of formula II or the preferred meanings given above or denotes P-Sp or P'.

P' is preferably straight-chain or branched alkyl with 1 to 25 C atoms which may be unsubstituted, mono- or polysubstituted by halogen or CN, it being also possible for one or more non-adjacent CH$_2$ groups to be replaced, in each case independently from one another, by —O—, —S—, —NH—, —N(CH$_3$)—, —CO—, —COO—, —OCO—, —OCO—O—, —S—CO—, —CO—S—, —CH=CH— or —C≡C— in such a manner that oxygen atoms are not linked directly to one another, and which is substituted with at least two identical or different polymerisable groups P as defined above.

Especially preferably P' is a group selected from -Sp-OCO—CR⁰(CH$_2$—OCO—CW=CH$_2$)$_2$ and -Sp-OCO—C (CH$_2$—OCO—CW=CH$_2$)$_3$, with Sp, W and R⁰ having the meanings given above, and R⁰ preferably being H or methyl.

In case one of the groups P, P', Sp, X, $A^{1-2}$, $Z^{1-3}$, R, R', R⁰, R⁰⁰ and T appears more than once in a formula as shown above and below, the multiple groups may be identical or different, unless explicitly stated otherwise.

The compounds of formula I can be synthesized according to or in analogy to methods that are known to the skilled in the art and described in the literature.

A further preferred embodiment of the present invention relates to compounds of formula I, wherein T is selected of formula II or the preferred subformulae II1-II9 shown above, wherein at least one of A¹ and A² is a naphthalene-2,6-diyl group, a difluoroterphenylene group or a diphenylacetlyene group that is optionally substituted by L. Some of these compounds are known from U.S. Pat. No. 5,723,066, for example those disclosed in example 1 and 2 therein, and from GB 2,351,734 A. The novel compounds of this preferred embodiment that are not disclosed in the above documents are another aspect of the invention. Further aspects of the invention are mixtures and polymers prepared from the known and the novel compounds of this preferred embodiment, and the use of these known and novel compounds, mixtures and polymers for organic semiconductor applications as described above and below. Especially preferred compounds of this type are those of the following subformulae:

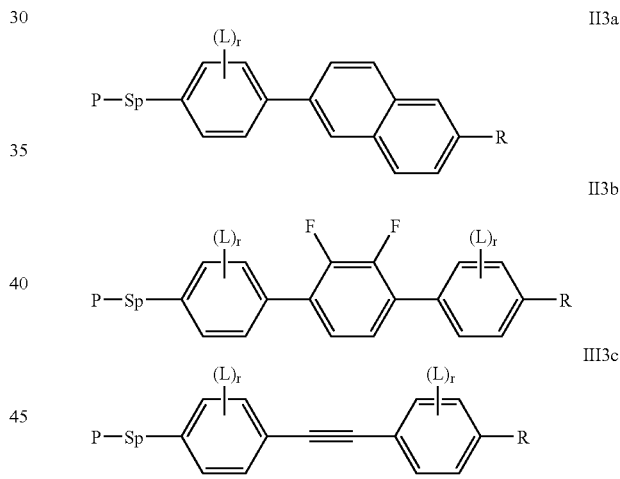

wherein P and Sp have the meanings given in formula I, L is as defined above, r is 0, 1, 2, 3 or 4, and R has the meaning given in formula II and is preferably P-Sp.

A further aspect of the invention relates to both the oxidised and reduced form of the compounds and materials according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(Cl_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g. $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Br), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns of tracts in electronic applications such as printed circuit boards and condensers.

The compounds of formula I can be polymerised, or copolymerised with other polymerisable compounds, via the polymerisable group P. This is preferably done by in-situ polymerisation of a coated layer of the material, preferably during fabrication of the electronic or optical device comprising the compound of formula I. In case of liquid crystal materials, these are preferably aligned in their liquid crystal state into homeotropic orientation prior to polymerisation, where the conjugated pi-electron systems are orthogonal to the direction of charge transport. This ensures that the intermolecular distances are minimised and hence then energy required to transport charge between molecules is minimised. The molecules are then polymerised or crosslinked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45-66

Alignment of the liquid crystal material can be achieved for example by treatment of the substrate onto which the material is coated, by shearing the material during or after coating, by application of a magnetic or electric field to the coated material, or by the addition of surface-active compounds to the liquid crystal material. Reviews of alignment techniques are given for example by 1. Sage in "Thermotropic Liquid Crystals", edited by G. W. Gray, John Wiley & Sons, 1987, pages 75-77, and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement 1 (1981), pages 1-77.

Polymerisation takes place by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerisable materials with acrylate or methacrylate groups, preferably a radical photoinitiator is used, when curing polymerisable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerisable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

The compounds of formula I can also be copolymerised with polymerisable mesogenic compounds to induce, or, in case of mesogenic materials of formula I, enhance liquid crystal phase behaviour. Polymerisable mesogenic compounds that are suitable as comonomers are known in prior art and disclosed for example in WO 93/22397; EP 0,261,712; DE 195,04,224; WO 95/22586 and WO 97/00600.

SCLCPs can be prepared from the polymerisable compounds or mixtures according to the invention by the methods described above, or by conventional polymerisation techniques which are known to those skilled in the art, including for example radicalic, anionic or cationic chain polymerisation, polyaddition or polycondensation. Polymerisation can be carried out for example as polymerisation in solution, without the need of coating and prior alignment, or polymerisation in situ. It is also possible to form SCLCPs by grafting compounds according to the invention with a suitable reactive group, or mixtures thereof, to presynthesized isotropic or anisotropic polymer backbones in a polymeranaloguous reaction. For example, compounds with a terminal hydroxy group can be attached to polymer backbones with lateral carboxylic acid or ester groups, compounds with terminal isocyanate groups can be added to backbones with free hydroxy groups, compounds with terminal vinyl or vinyloxy groups can be added e.g. to polysiloxane backbones with Si—H groups. It is also possible to form SCLCPs by copolymerisation or polymeranaloguous reaction from the inventive compounds together with conventional mesogenic or non mesogenic comonomers. Suitable comonomers are known to those skilled in the art. In principle it is possible to use all conventional comonomers known in the art that carry a reactive or polymerisable group capable of undergoing the desired polymer-forming reaction, like for example a polymerisable or reactive group P as defined above. Typical mesogenic comonomers are for example those mentioned in WO 93/22397; EP 0,261,712; DE 195,04,224; WO 95/22586 and WO 97/00600. Typical non mesogenic comonomers are for example alkyl mono- or diacrylates or alkyl mono- or dimethacrylates with alkyl groups of 1 to 20 C atoms, like methyl acrylate or methyl methacrylate, trimethylpropane trimethacrylate or pentaerythritol tetraacrylate.

The compounds of formula I and the polymerisable mixtures and polymers obtained thereof are useful as optical, electronic and semiconductor materials, in particular as charge transport materials in field effect transistors (FETs) e.g. as components of integrated circuitry, ID tags or TFT applications. Alternatively, they may be used in organic light emitting diodes (OLEDs) in electroluminescent display applications or as backlight of e.g. liquid crystal displays, as photovoltaics or sensor materials, and for other semiconductor applications, as electrode materials in batteries, as photoconductors and for electrophotographic applications like electrophotographic recording.

FETs comprising compounds of formula I or mixtures or polymers comprising them are suitable for example as ID tags in clothing, on food containers to register when food is out of date, on consumer products, household objects or any item which can be bought in a shop so that each item does not have to be priced individually, but for example many items can be passed through a reader at a till and all of the items in a shopping trolley can be registered at the same time, saving manpower and time.

Especially the oligomers and polymers according to the invention show advantageous solubility properties which allow production processes using solutions of these compounds. Thus films, including layers and coatings, may be generated by low cost production techniques e.g. spin coating. Suitable solvents or solvent mixtures comprise alkanes and/or aromatics, especially their fluorinated derivatives.

The materials of the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semiconductive material is arranged as a film between a gate-dielectric and a drain and a source electrode, are generally known e.g. from U.S. Pat. No. 5,892,244, WO 00/79617, U.S. Pat. No. 5,998,804, and from the references cited in the background and prior art chapter and listed below. Due to the advantages, like low cost production using the solubility properties of the compounds according to the invention and thus the processibility of large surfaces, preferred applications of these FETs are such as integrated circuitry, TFT-displays and security applications.

In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with money value, like stamps, tickets, shares, cheques etc.

Alternatively, the mono-, oligo- and polymers according to the invention may be used in organic light emitting devices or diodes (OLEDs), e.g. in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see e. g. Meerholz, Synthetic Materials, 111-112, 2000, 31-34, Alcala, J. Appl. Phys., 88, 2000, 7124-7128 and the literature cited therein.

According to another use, the inventive compounds, materials or films, especially those which show photoluminescent properties, may be employed as materials of light sources, e.g. of display devices such as described in EP 0 889 350 A1 or by C. Weder et al., Science, 279, 1998, 835-837.

Furthermore, the compounds of the present invention are useful as high birefringence compounds added to liquid crystalline compositions in order to increase birefringence. For this purpose, they do not need to have a mesophase themselves, but a similar shape to conventional liquid crystals in order to dissolve and not to detract from the liquid crystal properties of the composition.

In the foregoing and in the following examples, unless otherwise indicated, all temperatures are set forth uncorrected in degrees Celsius and all parts and percentages are by weight.

The following abbreviations are used to illustrate the liquid crystalline phase behaviour of the compounds: K=crystalline; N=nematic; S=smectic; Ch=cholesteric; I=isotropic. The numbers between the symbols indicate the phase transition temperatures in °C. Furthermore, mp. is the melting point, $\Delta n$ is the optical anisotropy measured at 20° C. and 589 nm, $\Delta\epsilon$ is the dielectric anisotropy at 20° C. and 1 kHz.

EXAMPLE 1

Compound (3) was prepared as described below

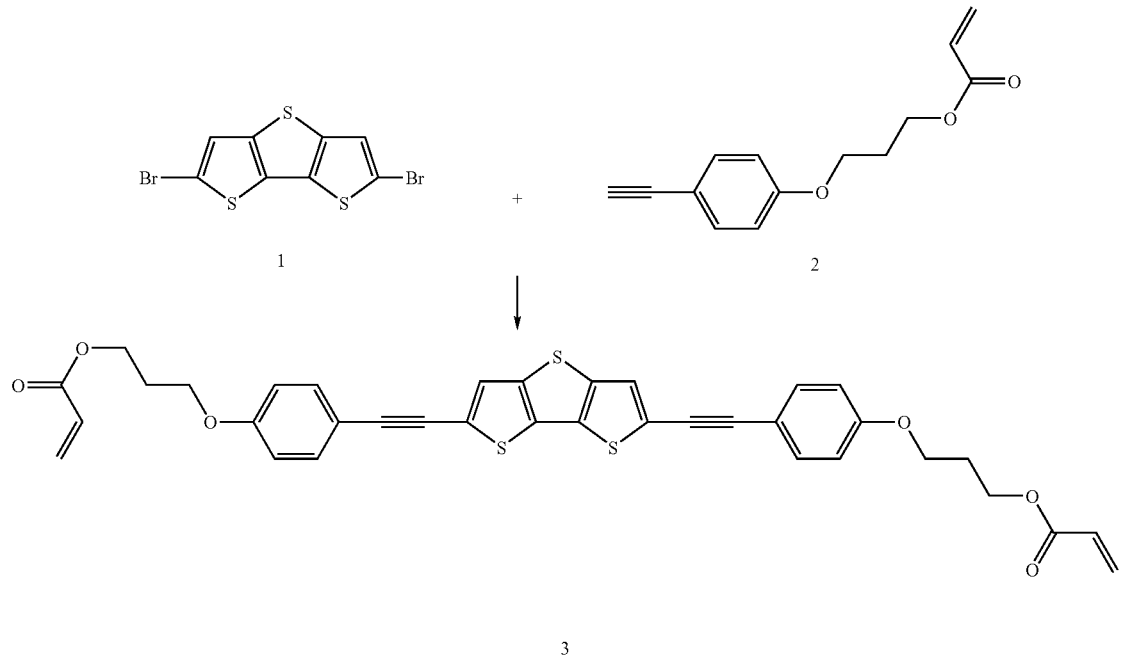

Acetylene -compound (2) (1.34 g, 5.82 mmol) in THF was added dropwise to a solution of 2,2'dibromod-ithienothiophene (1) (0.68 g, 1.94 mmol), triethylamine (20 ml), Pd(PPh$_3$)$_2$Cl$_2$ (catalytic) and

EXAMPLE 3

Compound (7) was prepared as described below

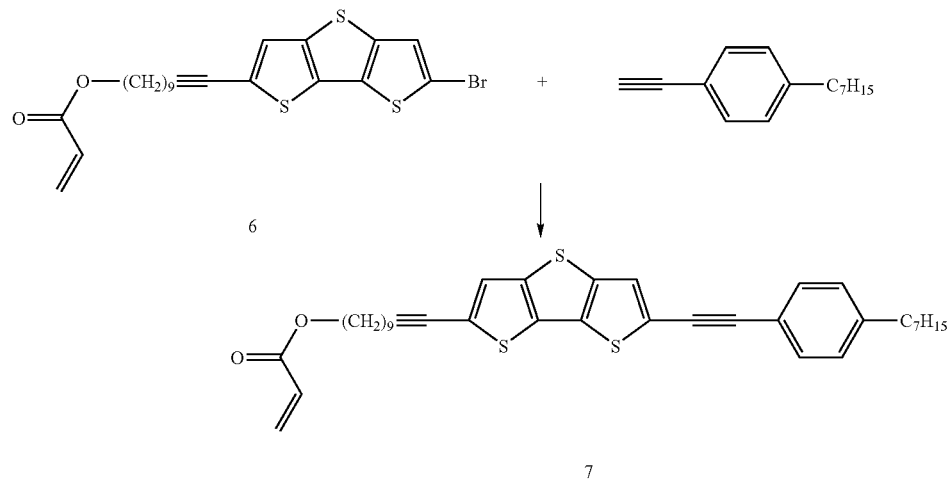

4-Heptylphenylacetylene (1.1 g, 5.47 mmol) in THF was added dropwise to a solution of DTT compound (6) (2.71 g, 5.47 mmol), triethylamine (20 ml), Pd(PPh$_3$)$_2$Cl$_2$ (catalytic)

and copper (1) iodide (catalytic) in THF (30 ml) under an atmosphere of nitrogen over a period of 2 hours at 40° C. After 16 h, the solution was allowed to cool to room temperature. The solution was poured in to dichloromethane and washed with water. The DCM layer was removed, dried over sodium sulphate and evaporated to dryness to leave a residual black solid. Purification was achieved by flash column chromatography using DCM:petrol (1:1). On evaporation of the appropriate fractions a yellow solid (0.5 g) was isolated.

$^1$H and $^{13}$C NMRs showed expected signals.

The following transitions and phases were observed by optical microscopy using crossed polarisers:

K-64-I

EXAMPLE 4

Compound (8) was prepared as described below

The following transitions and phases were observed by optical microscopy using crossed polarisers:
K-66-$S_B$-71-$S_A$-200-polymerises

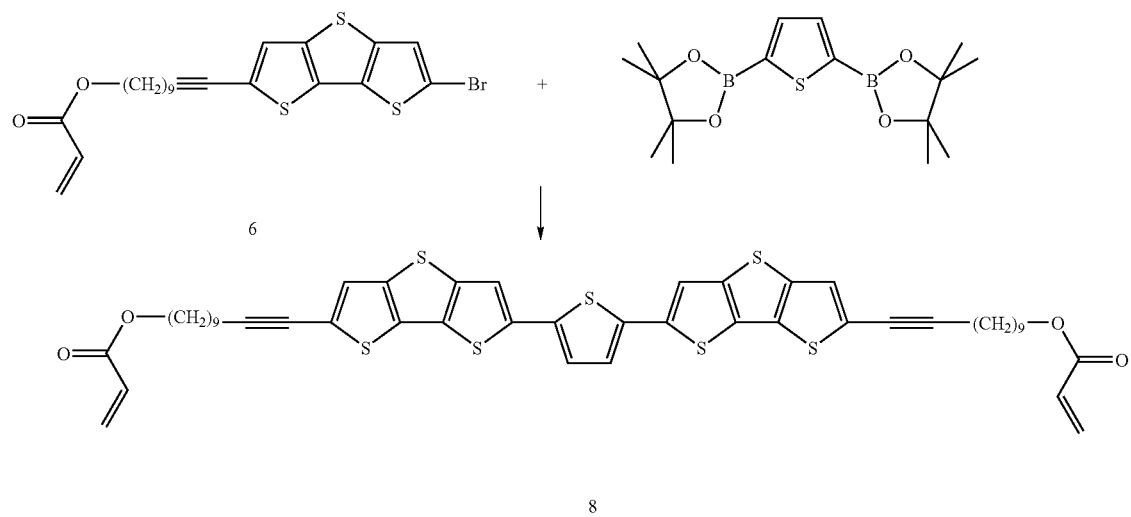

Thiophene bisboronate pinacol ester (0.57 g, 1.7 mmol) in THF was added dropwise to a solution of DTT compound (6) (1.68 g, 3.4 mmol) in toluene (30 ml), ethanol (30 ml), Pd(PPh$_3$)$_2$Cl$_2$ (catalytic) and sodium carbonate (0.72 g, 6.8 mmol) in water (20 ml) under an atmosphere of nitrogen over a 16 hours at reflux. The solution was allowed to cool to room temperature. The solution was poured in to dichloromethane and washed with water. The DCM layer was removed, dried over sodium sulphate and evaporated to dryness to leave a residual black solid. Purification was achieved by flash column chromatography using DCM: petrol (1:1). On evaporation of the appropriate fractions an orange solid (0.34 g) was isolated.

$^1$H and $^{13}$C NMRs showed expected signals.

EXAMPLE 5

Compound (10) was prepared as described below

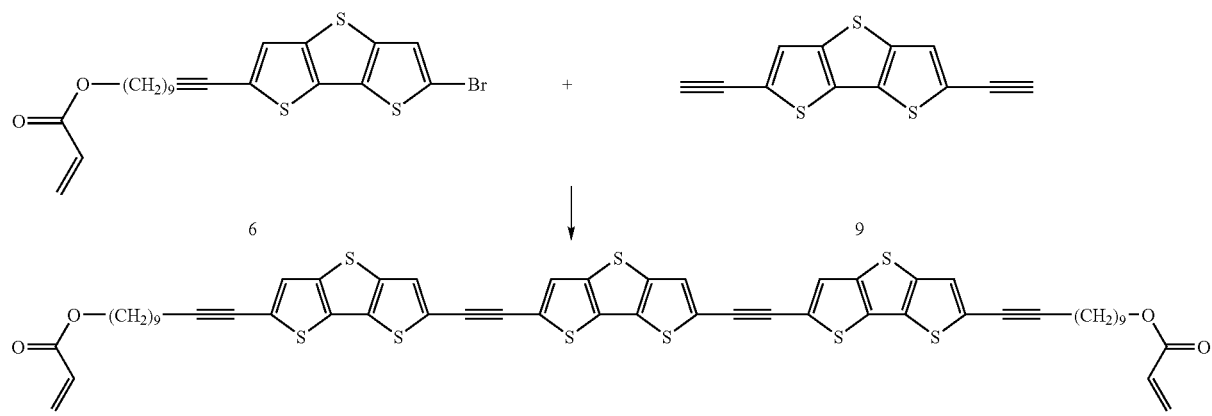

DTT-bis acetylene compound (9) (0.9 g, 3.69 mmol) in THF was added dropwise to a solution of DTT compound (6) (3.65 g, 7.38 mmol), triethylamine (20 ml), Pd(PPh$_3$)$_2$Cl$_2$ (catalytic) and copper (1) iodide (catalytic) in THF (30 ml) under an atmosphere of nitrogen over a period of 2 hours at 40° C. After 16 h, the solution was allowed to cool to room temperature. The solution was poured in to dichloromethane and washed with water. The DCM layer was removed, dried over sodium sulphate and evaporated to dryness to leave a residual black solid. Purification was achieved by flash column chromatography using DCM:petrol (4:1). On evaporation of the appropriate fractions a red solid (0.32 g) was isolated.

$^1$H and $^{13}$C NMRs showed expected signals.

The following transitions and phases were observed by optical microscopy using crossed polarisers:
K-112-S-212-decomposed

We claim:

1. A semiconductor material comprising a polymerisable charge transport compound comprising a group containing a delocalised pi-electron unit that imparts charge transport capability to the compound, and further comprising two or more polymerisable groups that are optionally linked to the group containing the delocalised pi-electron unit via flexible spacer groups.

2. A semiconductor material according to claim 1, wherein the group containing a delocalised pi-electron unit is a mesogenic group.

3. A semiconductor material according to claim 1, wherein the charge transport compound is of formula I $$(P\text{---}Sp)_{a\text{-}T} \qquad\qquad I$$

wherein
P is a polymerisable or reactive group,
Sp is a spacer group or a single bond,
a is an integer $\geq 2$, and
T is an optionally mesogenic group containing a delocalised pi-electron unit that imparts charge transport capability to the compound of formula I.

4. A semiconductor material according to claim 3, wherein T is of formula II $$\text{-}(Z^1\text{-}A^1)_m\text{-}(Z^2\text{-}A^2)_n\text{-}Z^3\text{-} \qquad\qquad II$$

wherein
$A^1$ is, in case of multiple occurrence independently of each other, an aromatic or heteroaromatic group, or a partially saturated alicyclic or heterocyclic group that is capable of forming a conjugated pi-electron system, having up to 25C atoms and being unsubstituted or mono- or polysubstituted with R,
$A^2$ has one of the meanings of $A^1$ or is, in case of multiple occurrence independently of each other, a saturated alicyclic or heterocyclic group with up to 25 C atoms which is unsubstituted, mono- or polysubstituted with R,
$Z^1$ to $Z^3$ are independently of each other —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C—, —CH=CH—COO—, —OCO—CH=CH— or a single bond,
$X^1$ and $X^2$ are independently of each other H, F, Cl or CN,
R is H, halogen, CN, NO$_2$, straight chain, branched or cyclic alkyl with 1 to 20 C-atoms, which is unsubstituted, mono- or poly-substituted by F, Cl, Br, I or CN, wherein one or more non-adjacent CH$_2$ groups are optionally replaced, in each case independently from one another, by —O—, —S—, —NH—, —NR$^0$—, SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, or is an aromatic or heteroaromatic group, or is P-Sp, $R^0$ and $R^{00}$ are independently of each other H or alkyl with 1 to 12 C-atoms,
m is 1, 2 or 3, and
n is 0, 1, 2 or 3.

5. A semiconductor material according to claim 3, wherein
P is CH$_2$=CW$^1$—COO—,

, 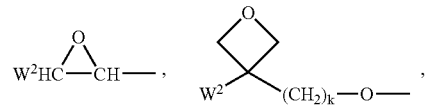,

CH$_2$=CW$^2$—(O)$_{k1}$—, CH$_3$—CH=CH—O—, HO—CW$^2$W$^3$—, HS—CW$^2$W$^3$—, HW$^2$N—, HO—CW$^2$W$^3$—, —NH—, CH$_2$=CW$^1$—CO—NH—, CH$_2$=CH—(COO)$_{k1}$—Phe-(O)$_{k2}$—, Phe-CH=CH—, HOOC—, OCN—, and W$^4$W$^5$W$^6$Si—,
wherein
$W^1$ is H, Cl, CN, phenyl or alkyl with 1 to 5 C-atoms,
$W^2$ and $W^3$ are independently of each other H or alkyl with 1 to 50C-atoms,
$W^4$, $W^5$ and $W^6$ are independently of each other Cl, oxaalkyl or oxacarbonylalkyl with 1 to 5 C-atoms,
Phe is 1,4-phenylene and
$k_1$ and $k_2$ are independently of each other 0 or 1.

6. A semiconductor material according to claim 1 wherein the charge transport compound is mesogenic or liquid crystalline.

7. A semiconductor material of claim 1 which is a polymerisable liquid crystal material of claim 1 and further comprising one or more other polymerizable compounds, wherein at least one of the polymerizable charge transport compounds of claim 1 and the further other polymerizable compound is mesogenic or liquid crystalline.

8. An anisotropic polymer film having charge transport properties comprising a semiconductor material according to claim 7 wherein said material comprises a liquid crystal mixture which is aligned in its liquid crystal phase into macroscopically uniform orientation and polymerized or crosslinked to fix the oriented state.

9. A semiconductor material comprising a side chain liquid crystal polymer obtained by polymerization of a semi-conductor material according to claim 1 or by grafting one or more compounds or a semiconductor material of claim 1 to a polymer backbone in a polymeranaloguous reaction, optionally with one or more additional mesogenic or non-mesogenic comonomers.

10. A field effect transistor (FET), OLED, electroluminescent device, RFID tag, backlight, photovoltaic or sensor device, photoconductor or electrophotographic recording device comprising a semiconductor material of claim 1 or a polymer thereof.

11. A security marking or a device comprising a semiconductor material of claim 1 or a polymer thereof.

12. A conducting ionic species comprising an oxidatively or reductively doped material, said material comprising a semiconductor material of claim 1 or a polymer thereof.

13. A charge injection layer, planarising layer, antistatic film or a conducting substrate or a pattern for electronic application or a flat panel display, comprising a conducting ionic species according to claim 12.

14. A security marking or device comprising a FET or RFID tag according to claim 10.

15. A semiconductor material of claim 3 wherein T is a rod-shaped, lath-shaped, or disk-shaped mesogenic group.

16. A semiconductor material of claim 3 wherein a is 2.

17. A semiconductor material of claim 4 wherein $Z^1$, $A^1$, $Z^2$, $A^2$ and $Z^3$ together form a conjugated pi-electron system.

18. A semiconductor material of claim 4 wherein
$A^1$ and $A^2$ are, independently of one another, an aromatic or heteroaromatic group and
$Z^1$, $Z^2$ and $Z^3$ are, independently of one another, a single bond, —C≡C— or —$CX^1$=$CX^2$—.

19. A semiconductor material of claim 4 wherein
$A^1$ and $A^2$ are, independently of one another, 1,4-phenylene wherein, one or more CH groups are optionally replaced by N, one or two non-adjacent $CH_2$ groups are optionally replaced by O and/or S, or is thiophene-2,5-diyl, thienothiophene-2,5-diyl, dithienothiophene-2,6-diyl or naphthalene-2,6-diyl group, which is unsubstituted, monosubstituted or polysubstituted by L, wherein
L is a halogen, CN, SCN, $NO_2$, $SF_5$ or an alkyl, alkoxy, alkylcarbonyl or alkoxycarbonyl group with 1 to 12 C atoms, wherein one or more H atoms are optionally substituted with F or Cl.

20. A semiconductor material of claim 19 wherein
$A^1$ and $A^2$ are, independently of one another, 1,4-phenylene which is substituted with 1, 2 or 3 L groups, or is thiophene-2,5-diyl, thienothiophene-2,5-diyl or dithienothiophene-2,6-diyl which are optionally substituted with one or more L groups.

21. A semiconductor material of claim 3 wherein P is an acrylate or oxetane group.

22. A semiconductor material of claim 3 wherein Sp is a spacer group of formula S—X, wherein
S is an alkylene with up to 20 C atoms which is unsubstituted, mono-substituted or poly-substituted by F, Cl, Br, I or CN, and wherein one or more non-adjacent $CH_2$ groups are optionally replaced, in each case independently from one another, by —O—, —S—, —NH—, —$NR^0$—, -$SiR^0R^{00}$—, —CO—, —COO—, —OCO—, —OCO—O—, —S—CO—, —CO—S—, —CH=CH— or —C≡C— in such a manner that O and/or S atoms are not linked directly to one another and
X is —O—, —S—, —CO—, —COO—, —OCO—, —O—COO—, —CO—$NR^0$—, —$NR^0$—CO—, $OCH_2$—, —$CH_2$O—, —$SCH_2$—, —$CH_2$S—, —$CF_2$O—, —$OCF2$—, —$CF_2$S—, —$SCF_2$—, —$CF_2CH_2$—, —$CH_2CF2$—, —$CF_2CF2$—, —CH=N—, —N=CH—, —N=N—, —CH=$CR^0$—, —$CX^1$=$CX^2$—, —C≡C—, —CH=CH—COO—, —OCO—CH=CH— or a single bond.

23. A semiconductor material of claim 4 wherein
$Z^1$, $Z^2$, and $Z^3$ are, independently of each other, —CH=N—, —N=CH—, —N=N—, —CH=$CR^0$—, —$CX^1$=$CX^2$—, —C≡C— or a single bond.

24. A semiconductor material of claim 4 wherein at least one of $A^1$ and $A^2$ is 1,4-phenylene, thiophene-2,5-diyl, thienothiophene-2,5-diyl or dithienothiophene-2,6-diyl which is optionally substituted with one or more L groups, wherein L is a halogen, CN, SCN, $NO_2$, $SF_5$ or an alkyl, alkoxy, alkylcarbonyl or alkoxycarbonyl group with 1 to 12 C atoms, wherein one or more H atoms are optionally substituted with F or Cl.

25. A semiconductor material of claim 24 wherein
P is $CH_2$=$CW^1$—COO—,

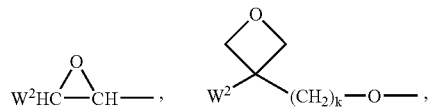

$CH_2$=$CW^2$—(O)$_{k1}$—, $CH_3$—CH=CH—O—, HO—$CW^2W^3$—, HS—$CW^2$—$W^3$—, H$W^2$N—, HO—$CW_2W^3$—NH—, $CH_2$=$CW^1$—CO—NH—, $CH_2$=CH—(COO)$_{k1}$—Phe-(O)$_{k2}$—, Phe-CH=CH—, HOOC—, OCN—, or $W^4W^5W^6$Si—,
wherein
$W^1$ is H, Cl, CN, phenyl or alkyl with 1 to 5 C-atoms,
$W^2$ and $W^3$ are independently of each other H or alkyl with 1 to 5 C-atoms,
$W^4$, $W^5$ and $W^6$ are independently of each other Cl, oxaalkyl or oxacarbonylalkyl with 1 to 5 C-atoms,
Phe is 1,4-phenylene and
$k_1$ and $k_2$ are independently of each other 0 or 1.

26. A semiconductor material of claim 24 wherein
$Z^1$ to $Z^3$ are independently of each other —CH=N—, —N=CH—, —N=N—, —CH=$CR^0$—, —$CX^1$=$CX^2$—, —C≡C— or a single bond.

27. A semiconductor material of claim 24 wherein
P is an acrylate or oxetane group.

28. A semiconductor material of claim 24 wherein Sp is a spacer group of formula S—X, wherein
S is an alkylene with up to 20 C atoms which is unsubstituted, mono-substituted or poly-substituted by F, Cl, Br, I or CN, and wherein one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡O— in such a manner that O and/or S atoms are not linked directly to one another and
X is —O—, —S—, —CO—, —COO—, —OCO—, —O—COO—, —CO—$NR^0$—, —$NR^0$—CO—, —$OCH_2$—, —$CH_2$O—, —$SCH_2$—, —$CH_2$S—, —$CF_2$O—, —$OCF_2$—, —$CF_2$S—, $SCF_2$—, $CF_2CH_2$—, —$CH_2CF_2$—, —$CF_2CF_2$—, —CH=N—, —N=CH—, —N=N—, —CH=$CR^0$—, —$CX^1$=$CX^2$—, —C≡C—, —CH=CH—COO—, —OCO—CH=CH— or a single bond.

29. A semiconductor material of claim 24 wherein
R is $C_1$-$C_{20}$-alkyl, $C_1$-$C_{20}$-fluoroalkyl, $C_1$-$C_{20}$-alkenyl, $C_1C_{20}$-alkynyl, $C_1$-$C_{20}$-alkoxy, $C_1$-$C_{20}$-thioether, $C_1$-$C_{20}$-silyl, $C_1$-$C_{20}$-ester and $C_1$-$C_{20}$-amino.

30. A semiconductor material of claim 5 wherein
$W^1$ is H, Cl or $CH_3$,
$W^2$ and $W^3$ are, independently of each other, methyl, ethyl or n-propyl.

* * * * *

UNITED STATES PATENT AND TRADEMARK OFFICE
CERTIFICATE OF CORRECTION

PATENT NO. : 7,329,896 B2  Page 1 of 1
APPLICATION NO. : 10/482937
DATED : February 12, 2008
INVENTOR(S) : Steven Tierney et al.

It is certified that error appears in the above-identified patent and that said Letters Patent is hereby corrected as shown below:

Column 19, line 21, reads "$(P-SP)_{a-T}$" should read --$(P-SP)_a$-T--
Column 19, line 63, reads "$SiR^0R^{00}$-," should read -- –$SiR^0R^{00}$— --
Column 20, line 18, reads "HO—$CW^2W^3$—, —NH—," should read --HO—$CW^2W^3$—NH—,--
Column 20, line 24, reads "1 to 50C-atoms." should read --1 to 5 C-atoms.--
Column 21, line 46, reads "$OCH_2$—," should read -- —$OCH_2$—,--
Column 21, line 47, reads "—$CF_2O$," should read -- —$CF_2O$—,--
Column 21, line 47, reads "—OCF2—," should read -- —$OCF_2$—,--
Column 21, line 48, reads "—$CH_2$CF2—," should read -- —$CH_2CF_2$—,--
Column 21, line 48, reads "—$CF_2$CF2—," should read -- —$CF_2CF_2$—,--
Column 22, line 16, reads "HO—$CW_2W^3$—NH—," should read -- HO—$CW^2W^3$—NH—,--
Column 22, line 42, reads "—C≡O—" should read -- —C≡C— --
Column 22, line 49, reads "$CF_2CH_2$—," should read -- —$CF_2CH_2$—,--
Column 22, line 55, reads "$C_1C_{20}$-alkynyl," should read --$C_1$-$C_{20}$-alkynyl,--

Signed and Sealed this

Twenty-ninth Day of June, 2010

David J. Kappos
*Director of the United States Patent and Trademark Office*